US008628723B2

(12) United States Patent
Vandergaw (10) Patent No.: US 8,628,723 B2
(45) Date of Patent: Jan. 14, 2014

(54) METHOD AND APPARATUS FOR SYRINGE-BASED SAMPLE INTRODUCTION WITHIN A FLOW CYTOMETER (75) Inventor: Angela L. Vandergaw, Fort Collins, CO (US)

(73) Assignee: Beckman Coulter, Inc., Brea, CA (US)

( * ) Notice: Subject to any disclaimer, the term of this patent is extended or adjusted under 35 U.S.C. 154(b) by 1043 days.

(21) Appl. No.: 12/684,801

(22) Filed: Jan. 8, 2010

(65) Prior Publication Data
US 2010/0112679 A1 May 6, 2010

Related U.S. Application Data (62) Division of application No. 11/190,300, filed on Jul. 27, 2005, now abandoned.

(51) Int. Cl.
G01N 33/00 (2006.01)
B01L 3/02 (2006.01)

(52) U.S. Cl.
USPC .............. 422/73; 422/68.1; 422/50; 422/400; 422/401; 422/402; 422/403; 422/404; 422/501; 422/504; 422/518; 422/521; 422/546; 422/564; 435/287.1; 435/287.3

(58) Field of Classification Search
USPC ............. 422/73, 67, 68.1, 50, 400–404, 422/500–501, 504, 508–509, 512, 518, 422/520–521, 546, 564; 435/287.1, 287.3
See application file for complete search history.

(56) References Cited

U.S. PATENT DOCUMENTS

| | | | |
|---|---|---|---|
| 3,935,883 A | 2/1976 | Stach et al. |
| 4,106,911 A | 8/1978 | Marcelli |
| 4,325,706 A | 4/1982 | Gershman et al. |
| 5,374,398 A | 12/1994 | Isami et al. |
| 5,431,201 A | 7/1995 | Torchia et al. |
| 5,439,645 A | 8/1995 | Saralegui et al. |
| 5,479,969 A | 1/1996 | Hardie et al. |
| 5,488,469 A | 1/1996 | Yamamoto et al. |
| 5,496,473 A | 3/1996 | Chow |
| 5,879,627 A | 3/1999 | Tanihata |

(Continued)

FOREIGN PATENT DOCUMENTS

EP 0046345 A2 2/1982

OTHER PUBLICATIONS

Zubkov and Burkill, "Syringe Pumped High Speed Flow Cytometry of Oceanic 18 Plankton", Cytometry Part A, vol. 69A, No. 9, Wiley Interscience, pp. 1010-1019, Sep. 1, 2006.

Primary Examiner — Brian R Gordon
(74) Attorney, Agent, or Firm — K&L Gates LLP; Louis C. Cullman (57) ABSTRACT An apparatus for introducing a specimen into a flow cytometer comprises: a syringe having a hollow barrel containing the specimen, a plunger partially within the barrel and a needle that extends into a volume of a nozzle of the flow cytometer; a one-way port in the nozzle forming a seal against the needle; a mounting platform coupled to both the syringe and to the flow cytometer; and a syringe pump coupled to the plunger, the syringe pump comprising a motor, a drive mechanism coupled to the motor; and a clamping mechanism coupled to the drive mechanism, wherein the motor operates the drive mechanism so as to cause the clamping mechanism to depress the plunger into the barrel.

20 Claims, 6 Drawing Sheets

(56) References Cited

U.S. PATENT DOCUMENTS

| | | | |
|---|---|---|---|
| 5,891,734 A | 4/1999 | Gill et al. | |
| 5,895,764 A | 4/1999 | Sklar et al. | |
| 6,387,330 B1 | 5/2002 | Bova et al. | |
| 6,473,171 B1 | 10/2002 | Buttry et al. | |
| 6,524,860 B1 | 2/2003 | Seidel et al. | |
| 6,551,277 B1 | 4/2003 | Ford | |
| 6,555,360 B1 | 4/2003 | Srienc et al. | |
| 6,604,435 B2 | 8/2003 | Buchanan et al. | |
| 6,638,481 B2 | 10/2003 | Sklar et al. | |
| 6,657,713 B2 | 12/2003 | Hansen | |
| 6,694,197 B1 | 2/2004 | Hatcher et al. | |
| 6,784,981 B1 | 8/2004 | Roche et al. | |
| 6,812,032 B1 * | 11/2004 | Carver et al. | 436/63 |
| 6,816,257 B2 | 11/2004 | Goix | |
| 6,878,556 B2 | 4/2005 | Sklar et al. | |
| 6,881,580 B2 | 4/2005 | Hall et al. | |
| 7,138,269 B2 * | 11/2006 | Blankenstein | 435/287.2 |
| 7,198,956 B2 | 4/2007 | Uffenheimer et al. | |
| 7,267,798 B2 | 9/2007 | Chandler | |
| 7,303,728 B2 | 12/2007 | Boillat et al. | |
| 7,410,809 B2 * | 8/2008 | Goix et al. | 436/518 |
| 7,459,126 B2 | 12/2008 | Okun | |
| 7,758,811 B2 * | 7/2010 | Durack et al. | 422/73 |
| 7,943,384 B2 * | 5/2011 | Durack et al. | 436/63 |
| 8,206,988 B2 * | 6/2012 | Durack et al. | 436/63 |
| 8,241,914 B2 * | 8/2012 | Durack et al. | 436/63 |
| 8,435,738 B2 * | 5/2013 | Holmes | 435/6.1 |
| 8,475,739 B2 * | 7/2013 | Holmes et al. | 422/509 |
| 8,486,347 B2 * | 7/2013 | Tajima | 422/501 |
| 2002/0028434 A1 | 3/2002 | Goix et al. | |
| 2002/0080341 A1 | 6/2002 | Kosaka | |
| 2002/0192113 A1 | 12/2002 | Uffenheimer et al. | |
| 2003/0030783 A1 | 2/2003 | Roche et al. | |
| 2003/0054558 A1 | 3/2003 | Kurabayashi et al. | |
| 2003/0143117 A1 | 7/2003 | Nagai et al. | |
| 2005/0036139 A1 | 2/2005 | Johnson | |
| 2005/0180885 A1 | 8/2005 | Tateishi et al. | |
| 2005/0249635 A1 | 11/2005 | Okun et al. | |
| 2005/0249642 A1 * | 11/2005 | Okun et al. | 422/103 |
| 2006/0141628 A1 | 6/2006 | Evans | |
| 2006/0281143 A1 | 12/2006 | Liu et al. | |
| 2007/0166195 A1 * | 7/2007 | Padmanabhan et al. | 422/68.1 |
| 2007/0189925 A1 | 8/2007 | Blecka et al. | |
| 2010/0173394 A1 * | 7/2010 | Colston et al. | 435/287.2 |

\* cited by examiner

METHOD AND APPARATUS FOR SYRINGE-BASED SAMPLE INTRODUCTION WITHIN A FLOW CYTOMETER

CROSS REFERENCE TO RELATED APPLICATIONS

This application is a divisional of U.S. application Ser. No. 11/190,300, filed Jul. 27, 2005, now abandoned, the disclosure of which is hereby incorporated by reference thereto in its entirety.

BACKGROUND OF THE INVENTION

1. Field of the Invention

The present invention relates to flow cytometers and flow cytometry for analyzing and sorting individual particles. More particularly, the present invention relates to sample introduction apparatus for a flow cytometer, the sample introduction apparatus including a syringe directly coupled to the flow cytometer.

2. Background Art

Flow cytometers have been in clinical and research use for many years. Basically, the systems act to position small amounts of a substance within a sheath fluid. This sheath fluid may either form droplets or may exist in a stream for optical analysis. Through hydrodynamic focusing and laminar flow, the sample is forced into a single file of individual cells and the like and is surrounded by a sheath fluid. In many applications, the sheath fluid together with its entrained substance exits a nozzle in a jet and either free falls or is channeled in an optically transparent pathway for analysis. Analysis and possible sorting of the particles as they traverse the optically transparent pathway have been employed in the determination of the variety of characteristics of individual particles. This analysis is most useful in analyzing or determining characteristics of biological cells for the collection of information which would be useful in areas of research, hematology, immunology and the like. The researcher, for example, may be interested in determining specific characteristics of the individual cells so that such cells may be classified, identified, quantified and perhaps sorted for further investigations or analysis.

Figure 1:
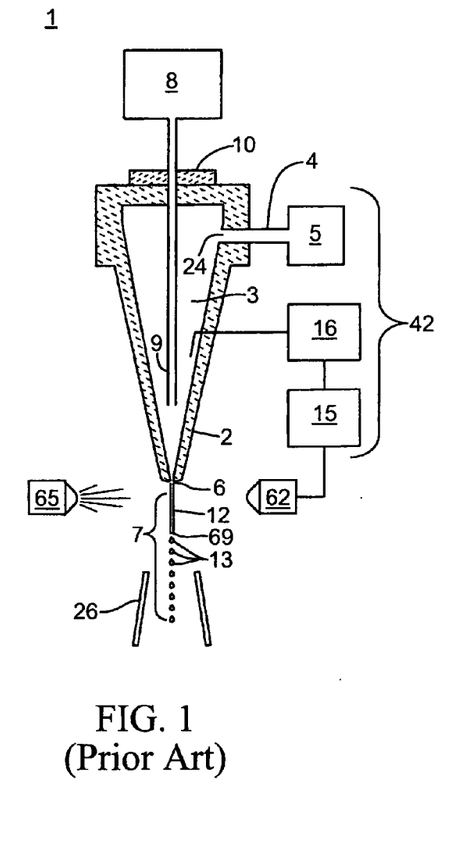
FIG. 1 is a schematic illustration of the operation of a conventional flow cytometer.

FIG. 1 is a schematic illustration of the operation of a typical flow cytometer. The flow cytometer 1 shown in FIG. 1 includes a nozzle system 42 that acts to introduce a flow of a substance within a sheath fluid. To accomplish this, the nozzle system 42 includes nozzle container 2 which establishes nozzle volume 3. The nozzle volume 3 has sheath fluid port 24 within it so that a sheath fluid may be introduced to it from a sheath reservoir 5 via a sheath fluid line 4. In addition, a substance introduction port 9 is included so that a substance may be introduced from substance reservoir 8 into the sheath fluid. The sheath fluid and its entrained substance are then hydrodynamically focused so that single cells and the like may be emitted from a nozzle tip 6 into free fall area 7 or an analysis area. By allowing the sheath fluid to exit from the nozzle volume 3, a jet 12 is created. This jet occurs within free fall area 7 or an analysis area where it may be analyzed or further processed.

In a sorting flow cytometer, as shown in FIG. 1, a vibration in jet 12 may be initiated by an oscillator 10. Oscillator 10 acts to initiate variations within jet 12 so that its oscillations may act to form droplets 13 from the sheath fluid at droplet separation point 69 as those skilled in the art readily understand. Each of the droplets 13 may be differentially analyzed in an analysis area to assess whether they contain a particular item or substance such as a cell or a cell fragment. For a sorting application, sorting equipment may be included to differentially charge each droplet which contains a cell or particle of interest and thus deflect them electrostatically. Typically, the sorting equipment comprises an electrical charging apparatus 16 including an electrode penetrating volume 3 and one or more electrostatic deflection plates 26. If oscillator 10 is not present or not operational, then the flow cytometer produces a continuous jet flow. In this case, the jet may simply be analyzed in an analysis area and collected in some receptacle for eventual disposal.

Importantly, most flow cytometers act to sense a specific property of the substance being analyzed. As shown in FIG. 1, this occurs through the use of some type of substance property sensor 62. Substance property sensor 62 may be positioned so that it senses light emissions occurring from the substance within jet 12. The signals then sensed may be utilized by analysis equipment 15 in a variety of different ways depending upon the particular substance or application involved. The light emissions from the substance may occur at one wavelength or frequency or may occur throughout a substance wavelength band. In order to analyze the substance, it is frequently common to cause the substance to fluoresce and then analyze its emissions. This may be created naturally or by stimulating the substance after it exits from nozzle container 2 through some type of substance stimulation source 65. Substance stimulation source 65 should be directed towards the substance possibly at location of jet 12. As those skilled in the art would readily understand, substance stimulation source 65 may emit electromagnetic radiation and thus serve as an electromagnetic source such as a laser which causes the substance to fluoresce. This fluorescence may occur within a fluorescence emission band.

Figure 2:
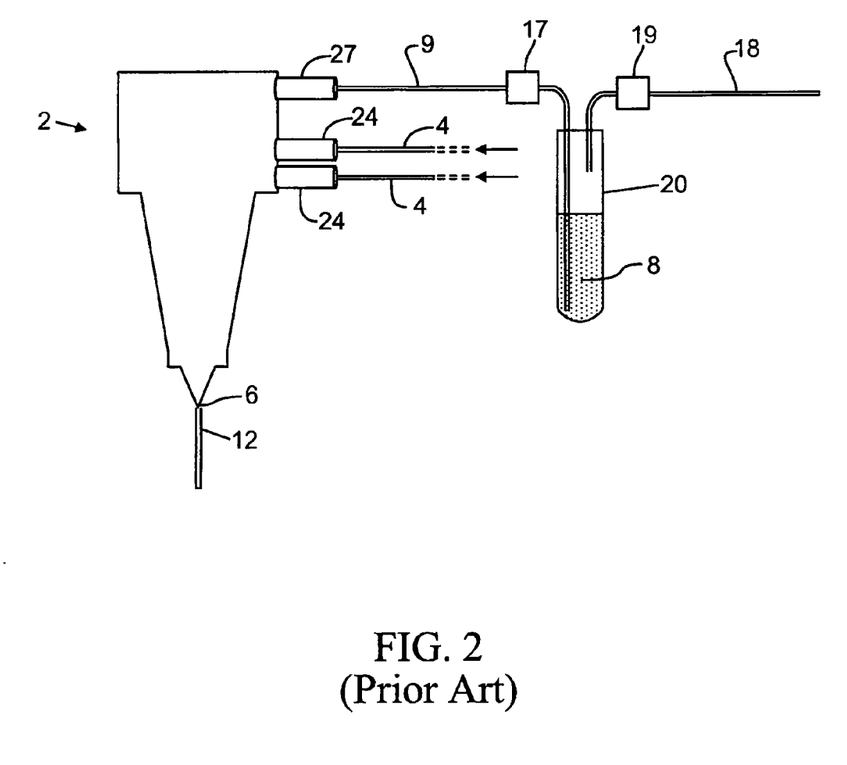
FIG. 2 is a schematic illustration of a conventional flow cytometer.

A known problem in the use of conventional flow cytometers arises from cross contamination between successive sample substances and contamination from non-sterile instrument parts. For example, FIG. 2 illustrates a portion of the fluidics system of a conventional flow cytometer. As illustrated in FIG. 2, the nozzle container 2 receives a sheath fluid received from sheath fluid lines 4 via sheath fluid ports 24 and receives a substance to be analyzed from substance introduction port 9 via a substance introduction port 9. Sheath fluid exits the nozzle container 2 through the nozzle tip 6. The reservoir 8 of the substance to be analyzed is contained within a pressurized container 20. Gas pressure is introduced into pressurized container 20 from gas line 18 and the pressure is controlled or shut off by gas pressure valve 19. The pressure in the container 20 forces the substance of the reservoir 8 to be forced into the substance introduction port 9 and the flow of the substance within the substance introduction port 9 is controlled or shut off by valve 17. Alternatively, instead of using a pressurized vessel 20, the sample substance may be caused to flow within the substance introduction port by means of a mechanical pump, such as a syringe pump.

Within the conventional flow cytometer diagrammatically illustrated in FIG. 2, to remove the reservoir comprising a first substance so that a second substance may be analyzed in its place, the valve 17 and the valve 19 are shut off so as to isolate the container 20. The container 20 is then replaced with another container having a reservoir of the second substance. Also, the substance introduction port 9 and the valve 17 must be either replaced or else thoroughly cleaned and sterilized. The non replaceable elements of the nozzle container 2 must be thoroughly flushed and sterilized. When replacing the various parts, such as the container 20 or the sample introduction port, care must also be exercised to ensure that the replacement parts are clean and sterile.

The above-described precautions that must be undertaken to prevent the contamination of an analyzed substance or to prevent cross contamination between substances can decrease the overall usage efficiency of a conventional flow cytometer. The exercise of these contamination precautions can also delay the start of and increase the costs of analyses obtained from the conventional flow cytometer. Occasionally, within clinical or hospital settings, important or even critical patient treatment decisions depend upon the rapid completion of analyses of biological samples, such as blood or other bodily fluids. Thus, inefficiencies in analytical capabilities can have detrimental health consequences for patients. Furthermore, these biological specimens are often withdrawn from a patient using a syringe and then subsequently transferred to holding vessels, such as the pressurized container 20 (FIG. 2) of a conventional flow cytometer. Each such transfer creates new opportunities for contamination or possible spoilage of the sample. Both time and contamination problems could be reduced if the specimen is transferred to the analytical instrument, such as a flow cytometer, in the same syringe used to obtain the specimen.

As a result of the above considerations, there is a need in the art for a simplified sample introduction system for a flow cytometer that eliminates many of the sample transfer lines, vessels and valves, that can reduce the preparation time required to initiate an analysis with the flow cytometer and that allows a greater number of samples to be analyzed in a given time with minimal contamination concerns. The present invention addresses such a need.

BRIEF SUMMARY OF THE INVENTION

In order to address the above-noted needs in the art of sample introduction to flow cytometers, a method and apparatus for improved sample introduction herein disclosed. The method and apparatus of the instant invention include syringe-based sample introduction to a flow cytometer.

A first object of the present invention is to provide a sample introduction apparatus for a flow cytometer that has the advantages of utilizing fewer components and occupying less space than are required within a conventional flow cytometer sample introduction apparatus. A second object of the present invention is to provide a sample introduction apparatus for a flow cytometer that has the advantage of reducing the opportunities for specimen contamination relative to conventional flow cytometer sample introduction apparatus. Another object of the present invention is to provide a sample introduction apparatus for a flow cytometer that has the advantages of increasing analytical efficiency and reducing preparation or set up time in relation to conventional flow cytometer sample introduction apparatus. Yet another object of the present invention is to provide a flow cytometer having an improved sample introduction apparatus that incorporates one or more of the advantages described above. A still further object of the present invention is to provide a method of sample introduction to a flow cytometer that provides one or more of the advantages described above.

The aforementioned objects and advantages are realized through the disclosure, herein of a method and apparatus for a syringe-based sample introduction system for a flow cytometer. A preferred embodiment, in accordance with the present invention, of a flow cytometer sample introduction apparatus comprises a syringe having a barrel portion containing the specimen, a plunger portion within the barrel portion and a needle portion that penetrates a nozzle container and extends into a nozzle volume of a flow cytometer; a one-way port in the nozzle container forming a seal against the syringe needle; a mounting platform coupled to both the syringe and to the flow cytometer; a syringe pump coupled to the syringe plunger portion and comprising a motor, a clamping mechanism and a drive mechanism; a pressure sensor coupled to a sheath fluid line of the flow cytometer; and a controller module electronically coupled to the pressure sensor and to the motor. The clamping mechanism of the syringe pump may be coupled to either a flange portion of the syringe barrel portion, to the mounting platform or to the flow cytometer itself. The controller module adjusts the force applied to the syringe plunger by the syringe pump in response to variations in sheath fluid pressure relayed to it by the pressure sensor, thereby maintaining a constant pressure differential between the sheath fluid and the analyzed substance.

A preferred embodiment, in accordance with the present invention, of a method for sample introduction to a flow cytometer comprises the steps of: providing a syringe having a barrel portion containing the specimen, a plunger portion within the barrel portion and a needle portion that penetrates a nozzle container and extends into a nozzle volume of a flow cytometer; providing a one-way port in the nozzle container forming a seal against the syringe needle; providing a mounting platform coupled to both the syringe and to the flow cytometer for holding the syringe in place relative to the flow cytometer; providing a syringe pump coupled to the syringe plunger portion and comprising a motor, a clamping mechanism and a drive mechanism; providing a pressure sensor coupled to a sheath fluid line of the flow cytometer; providing a controller module electronically coupled to the pressure sensor and to the motor; determining pressure variations in the sheath fluid with the pressure sensor and relaying electronic signals determined by the pressure variations to the controller module and transmitting control signals from the controller module to the motor so as to cause the syringe pump to depress the plunger at a controlled rate so as to deliver the specimen into the nozzle at an appropriate rate and a known volume.

DETAILED DESCRIPTION OF THE INVENTION

The present invention relates to an improved method and apparatus for sample introduction into a flow cytometer. The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiments shown but is to be accorded the widest scope consistent with the principles and features described herein. To more particularly appreciate the features and advantages of the method and apparatus of the present invention, the reader is referred to the appended FIGS. 3-6 in conjunction with the following discussion.

Figure 3:
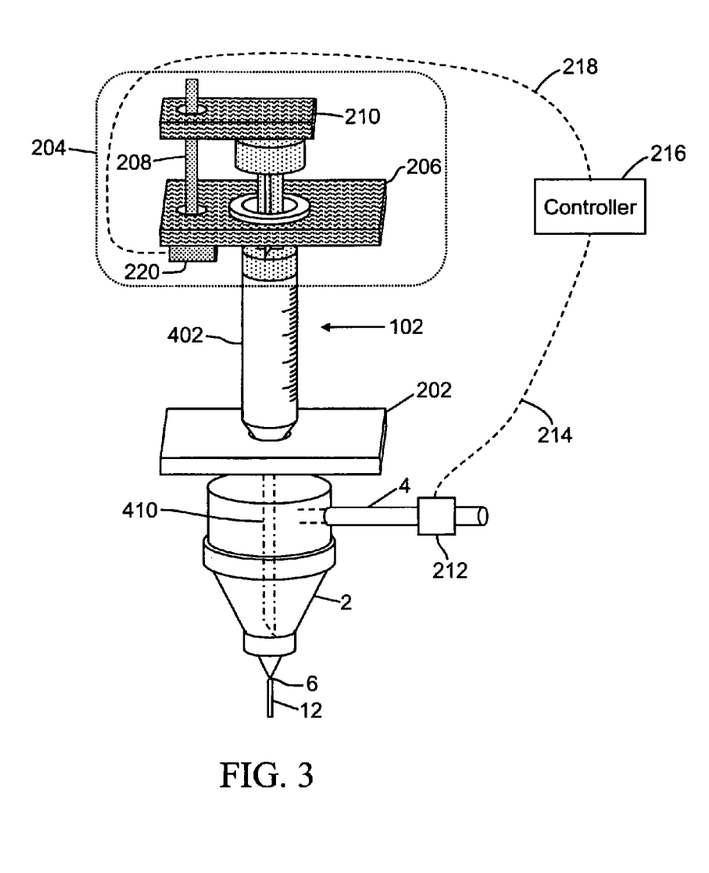
FIG. 3 is a schematic illustration of a first preferred embodiment of a sample introduction apparatus for a flow cytometer in accordance with the present invention.

FIG. 3 is a schematic drawing of a first preferred embodiment of a sample introduction apparatus for a flow cytometer in accordance with the present invention. The sample introduction apparatus comprises a conventional syringe 102 having a needle portion 410 that penetrates the nozzle container 2 and extends into an interior nozzle volume (not shown) within the nozzle container 2 via a one-way port (not shown) in the nozzle container 2, wherein the one-way port forms a seal against the needle portion 410. The end of the syringe needle 410 is positioned above the nozzle tip of the nozzle container 2 within the interior nozzle volume. The interior of the barrel portion 402 of the syringe 102 is filled with a sample substance, generally a suspension of particles in a liquid, the liquid containing or comprising particles that are to be analyzed in the flow cytometer. In the novel instant invention, the syringe barrel portion 402 is the substance reservoir 8 (FIG. 1) and the syringe needle replaces the conventional substance introduction port 9 (FIG. 1). The syringe 102 may be removed from the sample introduction apparatus and, in general, each substance to be analyzed will be introduced via its own respective syringe 102. In this fashion, cross contamination between different sample substances is minimized.

Figure 5:
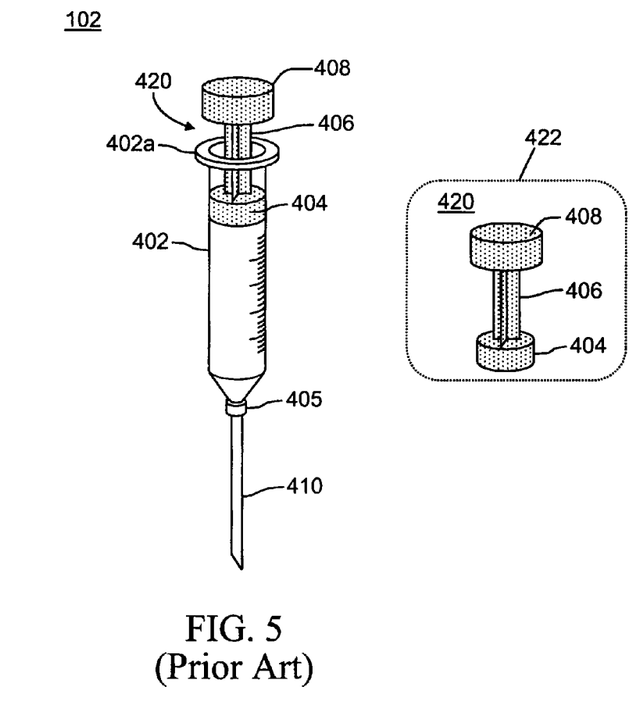
FIG. 5 is a diagram of a conventional syringe, with the various components labeled.

For clarity in discussion, FIG. 5 provides a drawing of a conventional syringe in isolation, with its various component parts labeled. The syringe 102 illustrated in FIG. 5 has a cylindrical barrel 402 with an outlet or nose 405 at its forward end and a flange or ear 402a at its rear end. As is commonly known, the syringe comprises a plunger 420, which is illustrated in greater detail in inset box 422, that is partially contained within the cylindrical barrel 402. A plunger gasket or pad 404 may be moved through the hollow interior of the barrel 402 by applying force upon plunger head 408 which drives plunger stem 406 and, consequently, plunger gasket or pad 404. Typically, the nose 405 may be connected to an replaceable influx and dispensing accessory, such as needle 410, or possibly a tubing (not shown) so that a liquid held within the cylindrical barrel 402 of the syringe can either be drawn into the syringe or dispensed out of the syringe.

Discussing, once again, the apparatus shown in FIG. 3, it may be observed that, in addition to the syringe, the novel sample introduction apparatus comprises a mounting platform 202 coupled to the flow cytometer for holding the syringe in place relative to the nozzle container 2, a syringe pump 204 for controlling sample introduction from the syringe 102 into the nozzle volume 3, a pressure sensor 212 disposed within the sheath fluid line 4 and a syringe pump controller 216 electronically coupled to the pressure sensor 212 via electrical line 214. The syringe pump 204 shown in FIG. 3 comprises a first plate 206 mechanically engaged to the flange 402a (FIG. 5), a second plate 210 engaged to the syringe plunger head 408 (FIG. 5), a conventional drive mechanism such as mechanical lead screw 208 engaged to both the first plate 206 and to the second plate 210 for applying a force that causes these two plates to approach one another and a motor 220 mechanically coupled to the drive mechanism 208. The motor 220 receives an electrical control signal from the controller 216 through electrical line 218. Preferably, the syringe pump 204 also comprises a force sensor, such as a spring device (not shown) between the second plate and the syringe plunger head, for monitoring the amount of force applied to the syringe plunger head by the syringe pump. This information on the applied force, together with the known cross sectional area of the syringe plunger pad (which is the same as the cross sectional area of the hollow internal portion of the syringe barrel 402) enables the pressure of the substance within the syringe to be calculated.

In a preferred method of operation of the instant sample introduction apparatus (FIG. 3), the syringe pump 204 slowly depresses the plunger head 408 and, thereby, the plunger gasket 404 of the syringe 102, thus injecting sample substance into the nozzle volume 3. The dispense of the sample is fully controllable through the operation of the controller 216 upon the motor 220, the controller 216 possibly being a computer that, through software, also controls or monitors the operation of other aspects of the flow cytometer to which the novel sample introduction apparatus is coupled. The pressure sensor 212 in the sheath fluid line 4 allows the controller to track the sheath fluid pressure and, consequently, the sheath fluid flow rate introduced into the nozzle container 2. In response to possible changing sheath flow rates, the controller may vary the rate of depression of or the amount of force applied to the syringe plunger, thus allowing the proper pressure differential, between the sheath fluid and the sample, to be maintained. Alternatively or additionally, the controller may vary or adjust the sheath fluid pressure in the sheath fluid line by conventional means such as regulating a pressure valve controlling a mechanical pump supplying the sheath fluid, controlling a gas pressure applied to a pressure vessel containing the sheath fluid reservoir, etc. In general, the sample fluid pressure should be approximately 0.1-0.3 pounds per square inch greater than the sheath fluid pressure. Because, in general, the amount of sample dispensed from the syringe 102 is precisely known for a known linear movement of the plunger 404 with respect to the barrel 402 (FIG. 5), the rate of volumetric sample introduction into the nozzle volume 3 may be precisely known or controlled. Further, if the particle density within the sample is known, then the absolute number of particle events-per-second through the nozzle of the flow cytometer may be calculated from the rate of volumetric sample introduction.

Because a new syringe is used for each respective sample, the need for special sample introduction lines and associated valves and reservoirs is eliminated and any cross-contamination between samples or contamination from non-sterile parts is minimized. To replace a first sample with a second sample, the user performs a method comprising the following sequence of steps:

Step 1. Disengage top plate 210 from syringe plunger head;
Step 2. Extract first syringe 102, containing first sample, from one-way port in nozzle container 2;
Step 3. Insert new syringe 2, containing second sample, into one-way port of nozzle container 2;
Step 4. Engage top plate with plunger head of second syringe;
Step 5. Optionally or as required, re-calibrate new lead screw position in controller software.

Figure 4:
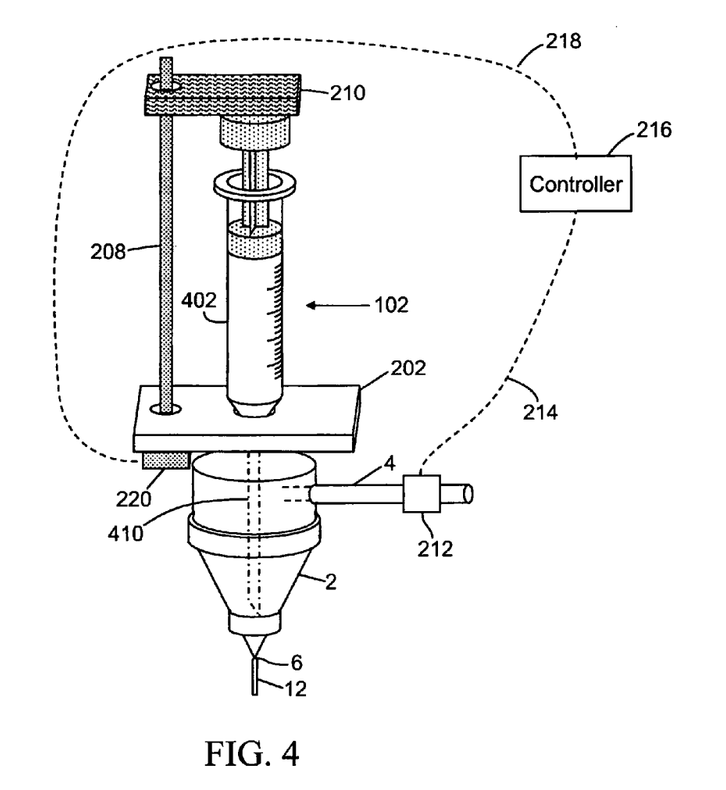
FIG. 4 is a schematic illustration of a second preferred embodiment of a sample introduction apparatus for a flow cytometer in accordance with the present invention.

FIG. 4 is a schematic drawing of a second preferred embodiment of a sample introduction apparatus for a flow cytometer in accordance with the present invention. The second preferred embodiment shown in FIG. 4 differs from the first preferred embodiment, already discussed with reference to FIG. 3, only in regards to the manner in which the syringe pump components are configured. In the preferred embodiment shown in FIG. 4, the motor 220 is engaged to the same mounting platform 202 that holds the syringe 102 in position relative to the nozzle container. Thus, the first plate 206 is eliminated and the drive mechanism passes through the mounting platform 202 and the second plate 210. The syringe pump mechanism illustrated in FIG. 4 also acts as a clamping mechanism for maintaining the syringe 102 immobile relative to the mounting platform 202.

Figure 6:
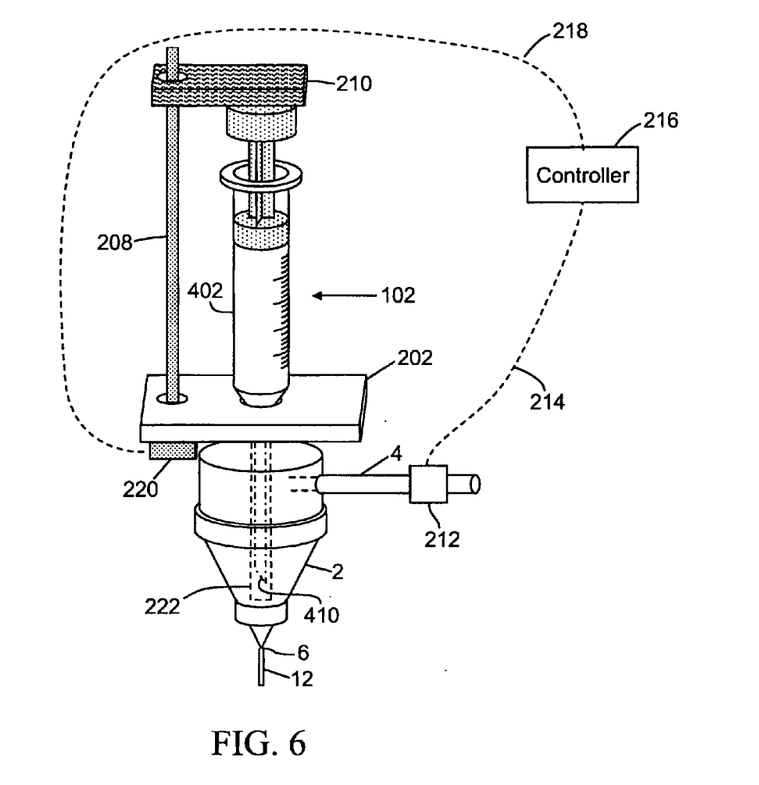
FIG. 6 is a schematic illustration of a third preferred embodiment of a sample introduction apparatus for a flow cytometer in accordance with the present invention.

FIG. 6 is a schematic illustration of a third preferred embodiment of a sample introduction apparatus for a flow cytometer in accordance with the present invention. The sample introduction apparatus shown in FIG. 6 is identical to that shown in and already discussed with reference to FIG. 4, except for the way in which the syringe needle is introduced into the nozzle volume. In the apparatus shown in FIG. 4, the syringe needle is directly introduced into the nozzle volume and operates as the substance introduction port 9 (FIG. 1). However, since there may be variations between the sizes or tip shapes of different syringe needles, it is not always possible to assure that the correct hydrodynamic focusing of sheath fluid with entrained substance particles will be consistently observed for all syringes. The sample introduction apparatus illustrated in FIG. 6 overcomes this problem through the use of a hollow receptacle 222 that resides within the nozzle volume and within which the syringe needle 410 fits. Preferably, the receptacle 222 has an interior gasket into which the syringe needle snugly fits and against which the needle forms a seal. The end of the receptacle is of the correct size and shape and at the correct location to assure proper hydrodynamic focusing. Since biological particles of the substance to be analyzed are introduced to the sheath fluid only from the end of the receptacle, changing from a first syringe needle to a second syringe needle does not affect the fluid flow properties as the jet exits the needle.

An improved method and apparatus for sample introduction into a flow cytometer have been disclosed and have been described according to some preferred explanatory embodiments. Those skilled in the art can now appreciate, from the foregoing description, that the broad techniques of the embodiments of the present invention can be implemented in a variety of forms. For instance, although specific configurations of syringe pumps have been discussed in regards to the preferred embodiments, it should be noted that a syringe pump, as utilized in the present invention, is, in its most basic form and need only be an adjustable clamping mechanism that is engaged, at a first end, to the plunger and that is also engaged, at a second end, to one of the syringe barrel, the mounting platform, or the flow cytometer. Therefore, while the embodiments of this invention have been described in connection with particular examples thereof, the true scope of the embodiments of the present invention should not be so limited since many variations and equivalents of the method and the apparatus may be carried out without departing from the scope of the invention as specified in the accompanying claims.

What is claimed is:

1. A specimen introduction system, comprising:
a flow cytometer having a nozzle;
a syringe, comprising: a hollow barrel for containing a specimen, a plunger partially disposed within the barrel, and a needle that extends into the nozzle;
a mounting platform coupled to the syringe;
a syringe pump, comprising:
a motor,
a drive mechanism coupled to the motor, and
a clamping mechanism coupled to the drive mechanism and the plunger; and
a control module operatively connected to the motor,
wherein the motor is adapted to operate the drive mechanism in response to a signal from the control module so as to cause the clamping mechanism to depress the plunger into the barrel and thereby introduce the specimen into the flow cytometer.

2. The system of claim 1, further comprising a hollow receptacle disposed within the nozzle for receiving the syringe needle.

3. The system of claim 2, further comprising a gasket disposed within the hollow receptacle.

4. The system of claim 1, wherein the clamping mechanism comprises:
a first plate coupled to the syringe; and
a second plate coupled to the plunger.

5. The system of claim 4, wherein the first plate is coupled to the syringe barrel.

6. The system of claim 4, wherein the first plate comprises the mounting platform.

7. The system of claim 1, further comprising:
a sheath fluid line operatively connected to the flow cytometer; and
a pressure sensor coupled to the sheath fluid line of the flow cytometer and the control module, and wherein the pressure sensor is configured to transmit a signal to the control module based upon a sheath fluid pressure in the sheath fluid line.

8. The system of claim 7, wherein the control module is configured to operate the motor in response to a signal to maintain a constant pressure differential between the sheath fluid pressure and a pressure of the specimen.

9. The system of claim 7, wherein the control module is configured to vary the sheath fluid pressure in response to a signal to maintain a constant pressure differential between the sheath fluid pressure and a pressure of the specimen.

10. The system of claim 1, wherein the drive mechanism comprises a lead screw.

11. A specimen introduction system, comprising:
a flow cytometer having a nozzle and a nozzle tip disposed at an end of the nozzle, and a sheath fluid line;
a syringe, comprising: a hollow barrel for containing a specimen, a plunger partially disposed within the barrel, and a needle disposed above the nozzle tip and extending into the nozzle;
a mounting platform coupled to the syringe;
a syringe pump, comprising:
a motor,
a drive mechanism coupled to the motor, and
a plate coupled to the drive mechanism; and
a control module operatively connected to the motor,
wherein the motor is adapted to operate the drive mechanism in response to a signal from the control module so as to cause the plate to translate toward the mounting platform and depress the plunger into the barrel, thereby introducing the specimen into the flow cytometer.

12. The system of claim 11, wherein the syringe barrel has an axis and the syringe needle extends linearly along the barrel axis into the nozzle.

13. The system of claim 11, wherein the syringe needle is straight.

14. The system of claim 11, further comprising a second plate, wherein the second plate is coupled to the barrel, the mounting platform, or the flow cytometer.

15. The system of claim 11, further comprising:
a sheath fluid line operatively connected to the flow cytometer; and
a pressure sensor coupled to the sheath fluid line and the control module, and wherein the pressure sensor is configured to transmit a signal to the control module based upon a sheath fluid pressure in the sheath fluid line.

16. A specimen introduction system, comprising:
a flow cytometer having a nozzle and a hollow receptacle disposed within the nozzle;
a syringe disposed above the flow cytometer, comprising:
a hollow barrel for containing a specimen,
a plunger partially disposed within the barrel, and
a needle that extends into the receptacle;
a mounting platform coupled to the syringe;
a syringe pump, comprising:
a motor,
a drive mechanism coupled to the motor, and
a clamping mechanism coupled to the drive mechanism and the plunger; and
a control module operatively connected to the motor,
wherein the motor is adapted to operate the drive mechanism in response to a signal from the control module so as to cause the clamping mechanism to depress the plunger into the barrel and thereby introduce the specimen into the flow cytometer.

17. The system of claim 16, further comprising a gasket disposed within the receptacle.

18. The system of claim 16, wherein the clamping mechanism comprises:
a first plate coupled to the syringe; and
a second plate coupled to the plunger.

19. The system of claim 18, wherein the first plate is coupled to the syringe barrel.

20. The system of claim 18, wherein the first plate comprises the mounting platform.

* * * * *